(12) United States Patent
Razouki

(10) Patent No.: US 11,617,514 B2
(45) Date of Patent: Apr. 4, 2023

(54) HANDS FREE HEART-BEAT AUDIO TRANSMITTER AND RECEIVER SYSTEM FOR EXERCISE, MEDITATION AND RELAXATION

(71) Applicant: Crystal Razouki, San Diego, CA (US)

(72) Inventor: Crystal Razouki, San Diego, CA (US)

(73) Assignee: Crystal Razouki, San Diego, CA (US)

(*) Notice: Subject to any disclaimer, the term of this patent is extended or adjusted under 35 U.S.C. 154(b) by 96 days.

(21) Appl. No.: 16/393,022

(22) Filed: Apr. 24, 2019

(65) Prior Publication Data

US 2019/0320919 A1 Oct. 24, 2019

Related U.S. Application Data

(60) Provisional application No. 62/662,067, filed on Apr. 24, 2018.

(51) Int. Cl.
*A61B 5/024* (2006.01)
*A61B 7/04* (2006.01)

(52) U.S. Cl.
CPC ............ *A61B 5/02438* (2013.01); *A61B 7/04* (2013.01)

(58) Field of Classification Search
CPC .............................................. A61M 2021/0061
USPC ............................................................ 600/28
See application file for complete search history.

(56) References Cited

U.S. PATENT DOCUMENTS

| | | | | |
|---|---|---|---|---|
| 4,021,933 A * | 5/1977 | Hughes | ............... | G09B 23/00 434/262 |
| 4,850,023 A * | 7/1989 | Yarush | ............... | A61B 7/04 381/67 |
| 4,898,179 A * | 2/1990 | Sirota | ............... | A61B 7/04 381/67 |
| 5,314,389 A | 5/1994 | Dotan | | |
| 5,807,268 A * | 9/1998 | Reeves | ............... | A61B 7/003 600/513 |
| 6,212,427 B1 * | 4/2001 | Hoover | ............... | A61B 5/0006 600/515 |
| 8,460,189 B2 | 6/2013 | Libbus et al. | | |
| D730,761 S | 6/2015 | Spaeth et al. | | |
| 10,631,786 B2 * | 4/2020 | Horii | ............... | A61B 7/04 |
| 2005/0074130 A1 * | 4/2005 | Brummel | ............... | A61B 7/04 381/67 |
| 2007/0203421 A1 * | 8/2007 | Cho | ............... | A61B 5/0002 600/519 |
| 2007/0299354 A1 * | 12/2007 | Striepe | ............... | A61B 5/02405 600/509 |
| 2008/0013747 A1 | 1/2008 | Tran | | |
| 2008/0114220 A1 | 5/2008 | Banet et al. | | |

(Continued)

OTHER PUBLICATIONS

Digi-Key, Spark fun electronics—https://www.digikey.com/product-detail/en/sparkfun-electronics/BOB-12758/1568-1472-ND/6592307?WT.srch=1&gclid=Cj0KCQjwzlzWBRDnARIsAAkc8hHMsZ1BMi9VEwb1ELMOZI9qCL-hEMINckX4SOJ1igo46pac3-V28K4aAjgNEALw_wcB, pub. at least by Apr. 20, 2018.

(Continued)

*Primary Examiner* — Kennedy Schaetzle

(74) *Attorney, Agent, or Firm* — Procopio, Cory, Hargreaves & Savitch LLP

(57) ABSTRACT

Disclosed is a hands-free heart-beat audio transmitter and receiver, plus related methods of meditation and relaxation. In one embodiment, the disclosed system is a device that allows a user to listen to his or her heartbeat wirelessly and hands-free during meditation and relaxation.

8 Claims, 2 Drawing Sheets

(56) References Cited

U.S. PATENT DOCUMENTS

| | | | |
|---|---|---|---|
| 2008/0171945 A1* | 7/2008 | Dotter | A61B 5/486 600/514 |
| 2008/0214903 A1 | 9/2008 | Orbach | |
| 2009/0177097 A1* | 7/2009 | Ma | A61B 5/14551 600/500 |
| 2010/0069735 A1 | 3/2010 | Berkner | |
| 2010/0172522 A1 | 7/2010 | Mooring et al. | |
| 2010/0240945 A1 | 9/2010 | Bikko | |
| 2013/0150754 A1* | 6/2013 | Rogers | A61B 7/04 600/586 |
| 2013/0253334 A1 | 9/2013 | Al-Ali et al. | |
| 2014/0142403 A1* | 5/2014 | Brumback | A61B 5/14532 600/479 |
| 2014/0303521 A1* | 10/2014 | Nakamura | A61B 7/003 600/586 |
| 2015/0057512 A1* | 2/2015 | Kapoor | A61B 5/0456 600/324 |
| 2015/0164340 A1* | 6/2015 | Bedingham | A61B 5/742 600/484 |
| 2017/0238812 A1* | 8/2017 | Atlas | A61B 5/1117 |
| 2017/0333666 A1* | 11/2017 | Goldberg | A61B 5/165 |
| 2018/0325487 A1* | 11/2018 | Hoppmann | A61B 8/56 |
| 2019/0298272 A1* | 10/2019 | Persen | A61B 5/02405 |
| 2019/0307983 A1* | 10/2019 | Goldman | A61B 5/165 |

OTHER PUBLICATIONS

Parafix, double sided tape, https://parafix.com/product-groups/double-sided-materials/double-sided-tape/ published at least by Apr. 20, 2018.

\* cited by examiner

HANDS FREE HEART-BEAT AUDIO TRANSMITTER AND RECEIVER SYSTEM FOR EXERCISE, MEDITATION AND RELAXATION

CROSS-REFERENCE TO RELATED APPLICATIONS

This application claims the benefit and priority of U.S. Prov. App. Ser. No. 62/662,067 filed on 24 Apr. 2018 and titled "Hands free heart-beat audio transmitter and receiver system, plus related methods of exercise, meditation and relaxation." That document is hereby incorporated by reference in its entirety.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO AN APPENDIX SUBMITTED ON A COMPACT DISC AND INCORPORATED BY REFERENCE OF THE MATERIAL ON THE COMPACT DISC

Not applicable.

STATEMENT REGARDING PRIOR DISCLOSURES BY THE INVENTOR OR A JOINT INVENTOR

Reserved for a later date, if necessary.

BACKGROUND OF THE INVENTION

Field of Invention

The disclosed subject matter is in the field of apparatus and related methods of meditation, exercise and relaxation. Specifically, the disclosed subject matter is in the field of heart-beat audio transmitter and receiver systems, plus related methods of using the transmitters and receivers to accomplish meditation or relaxation. Additionally, the disclosed subject matter is in the field of software applications for recording a user's heart beat for a predetermined period of time and playing back portions of the recorded heartbeat that demonstrate increased heart rate variability (i.e., play back of a portion of the user's heart beat that was recorded while the user was relaxed).

BACKGROUND OF THE INVENTION

Heart sounds are the noises generated by the heart muscle and resulting flow of blood caused by its contractions and expansions. The sounds created are directly caused by turbulent blood fluid and contraction and expansion of the muscle opens and closes valves to produce blood flow throughout the body. The heart has two distinct sounds that are produced by the alternating operation of the atrioventricular and semilunar heart valves. The first sound is produced when the atrioventricular valves of the heart muscle are closed and the semilunar valves are open. The second sound is produced when the semilunar valves are closed and the atrioventricular valves are open. Doctors often listen closely to the sounds of a patient's heart via a stethoscope to determine whether the heart is operating normally or is otherwise healthy.

In addition to doctors, other third-parties listen to another's heart sounds in nonmedical situations because the sounds of a beating heart are known to provide benefits to such third-party listeners. For instance, mothers often hold their newborn babies against their chest and it is thought that the sounds of the mothers heart, albeit feinted and dampened by the mother's chest tissue, soothe the baby and contributes to the baby's brain development. In another instance, after infancy, adolescent and adult lovers are known to listen to one-another's' heart sounds through the chest tissue as a bonding or intimacy-promoting exercise. A stethoscope can be used to increase the volume of a heart sounds to a third-party listener, but the struggle of holding the stethoscope in place detracts from the soothing or intimate nature of sounds. So, stethoscopes are not preferred by babies or lovers listening to heart sounds.

Monitoring your own heart beat is also beneficial. Heart rate monitors are worn by exercisers to ensure that their heart rate is within a desired range for weight loss. Individuals also often self-diagnose ailments by monitoring their heart rate. Finally, many methods of relaxation or meditation involve controlled breathing and heart rate monitoring to keep the heart rate to a preferred range. However, these heart monitoring techniques have not yet included the soothing and intimacy promoting benefits of listing to heart sounds. Many heart monitors detect the electrical pulses generated by a beating heart and in some prior art the electrical pulses have been set to sound, but these electrical pulses are not true representations of heart sounds. They are just beeps or other noses that go off when the art pumps. Of course, a stethoscope could be held against one's own chest to listen to the true heart sound during exercise, meditation, or relaxation, but the stethoscope is not hands free and, like with third party listeners, can detract from the soothing and intimate nature of listening to one's own heart sounds.

In view of the foregoing, a need exists for a hands-free heart-beat audio transmitter and receiver system, plus related methods of exercise, meditation and relaxation.

Listening to one's own heart beat can be relaxing. It has been determined that listening to a recording of one's own heart beat can also be relaxing when the recording was taken while in a relaxed state. According to firstbeat.com, higher heart rate variability has been found to be associated with reduced morbidity and mortality, and improved psychological well-being and quality of life. For purposes of this system, heartrate variability is defined as the physiological phenomenon of variation in the time interval between heartbeats, measured by the beat-to-beat interval. In normal healthy situations, heart rate variability increases during relaxing activities (like during meditation or sleep). As expected, heart rate variability decreases when a user is stressed out. Thus, a need further exists for apparatus and related methods of recording and playing back one's own heartbeat, including software for isolating and playing back portions of the recorded heart beat that manifest high heart rate variability.

RELATED ART

US20100172522A1 by Mooring et al. (circa 2010) discloses a "programmable earphone device with customizable controls and heartbeat monitoring."

US20100069735A1 by Berkner (circa 2010) discloses a "device for mobile electrocardiogram recording."
US20080013747A1 by Tran (circa 2008) discloses a "digital stethoscope and monitoring instrument."
U.S. Pat. No. 5,314,389 by Dotan (circa 1994) discloses an "exercise monitor."
US20080171945A1 by Dotter (circa 2008) discloses an "apparatus and method for measuring heart rate and other physiological data." T
US20100240945A1 by Bikko (circa 2010) discloses a "respiratory biofeedback devices, systems and methods."
US20080114220A1 by Banet et al. (circa 2008) discloses a "two-part patch sensor for monitoring vital signs."
U.S. Pat. No. 8,460,189 by Libbus et al. (circa 2013) discloses an "adherent cardiat monitor with advanced sensing capabilities."
US20130253334A1 by Al-Ali et al. (circa 2013) discloses a "wireless patient monitoring device."
US20080214903A1 by Orbach (circa 2008) discloses "methods and systems for physiological and psycho-physiological monitoring and uses thereof."
USD730761 by Spaeth et al. (circa 2015) discloses a "wearable sensor."

SUMMARY OF THE INVENTION

Disclosed is a hands-free heart-beat audio transmitter and receiver, plus related methods of meditation and relaxation. In one embodiment, the disclosed system is a device that allows a user to listen to his or her heartbeat wirelessly and hands-free during meditation and relaxation. In a preferred embodiment, a heart-monitor may be placed over the heart with a skin-compatible adhesive. Suitably, the heart monitor may be defined by a microphone and transmitter for picking-up the hearts original sound wave input, converting the original sound wave to an electronic audio signal, transmitting an electrical audio signal wirelessly to Bluetooth® headphones worn by the user. Suitably, the headphones feature a receiver and speaker that translates the audio signal to a digital sound output so that the listener can enjoy the sounds of his or her own beating heart. In another embodiment, the heart monitor includes a recorder and computer memory for storing a digital copy of the electronic audio signal for later transmission and playback of the headphones. In another embodiment, the heart monitor includes an audio jack for wired connection to the headphones.

BRIEF DESCRIPTION OF THE SEVERAL VIEWS OF THE DRAWINGS

Other objectives of the disclosure will become apparent to those skilled in the art once the invention has been shown and described. The manner in which these objectives and other desirable characteristics can be obtained is explained in the following description and attached figures in which.

It is to be noted, however, that the appended figures illustrate only typical embodiments of this invention and are therefore not to be considered limiting of its scope, for the invention may admit to other equally effective embodiments that will be appreciated by those reasonably skilled in the relevant arts. Also, figures are not necessarily made to scale but are representative.

DETAILED DESCRIPTION OF PREFFERED EMBODIMENTS

Disclosed is a hands-free heart-beat audio transmitter and receiver system, plus related methods of meditation and relaxation. In a preferred embodiment, the system includes a heart monitor and headphones. In one mode of use, the heart monitor is adhered to a user's chest and is configured to pick-up original sound wave inputs from the heart, convert the original wave into an audio signal, and record or transmit wirelessly or wired the audio signal to the headphones. In one mode of use, the headphones are configured to receive the audio signal input from the heart monitor, convert the signal into a digital soundwave output. When used, the system can enable a user to be soothed or comforted by self-intimacy during exercise, relaxation, or meditation. The more specific features of the disclosed system are disclosed in connection with the figures.

Figure 1:
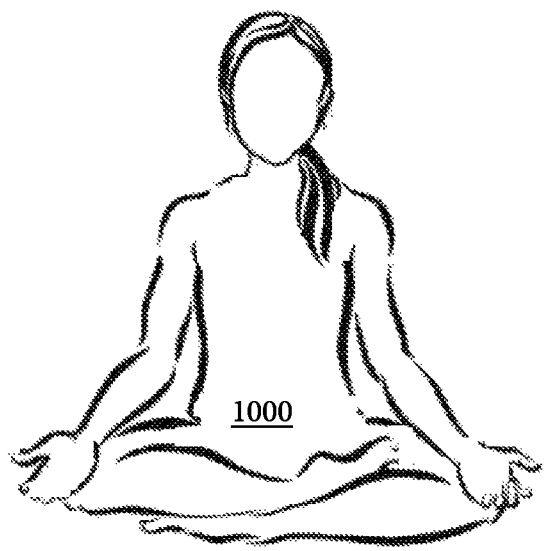
FIG. 1 is a basic view of a user 1000 meditating, relaxing, or exercising.
Figure 2:
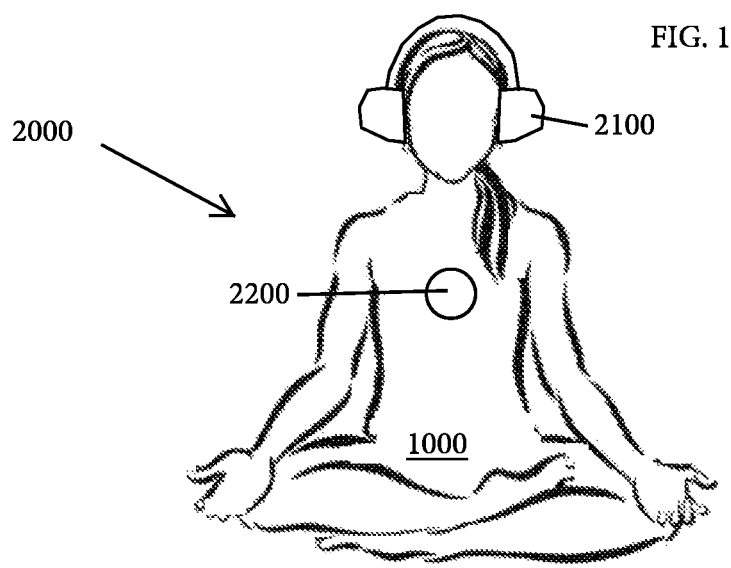
FIG. 2 is a basic view of the user 1000 meditating, relaxing, or exercising with a wireless and hands-free heart-beat audio transmitter and receiver system 2000 in position in the user 1000.
Figure 4:
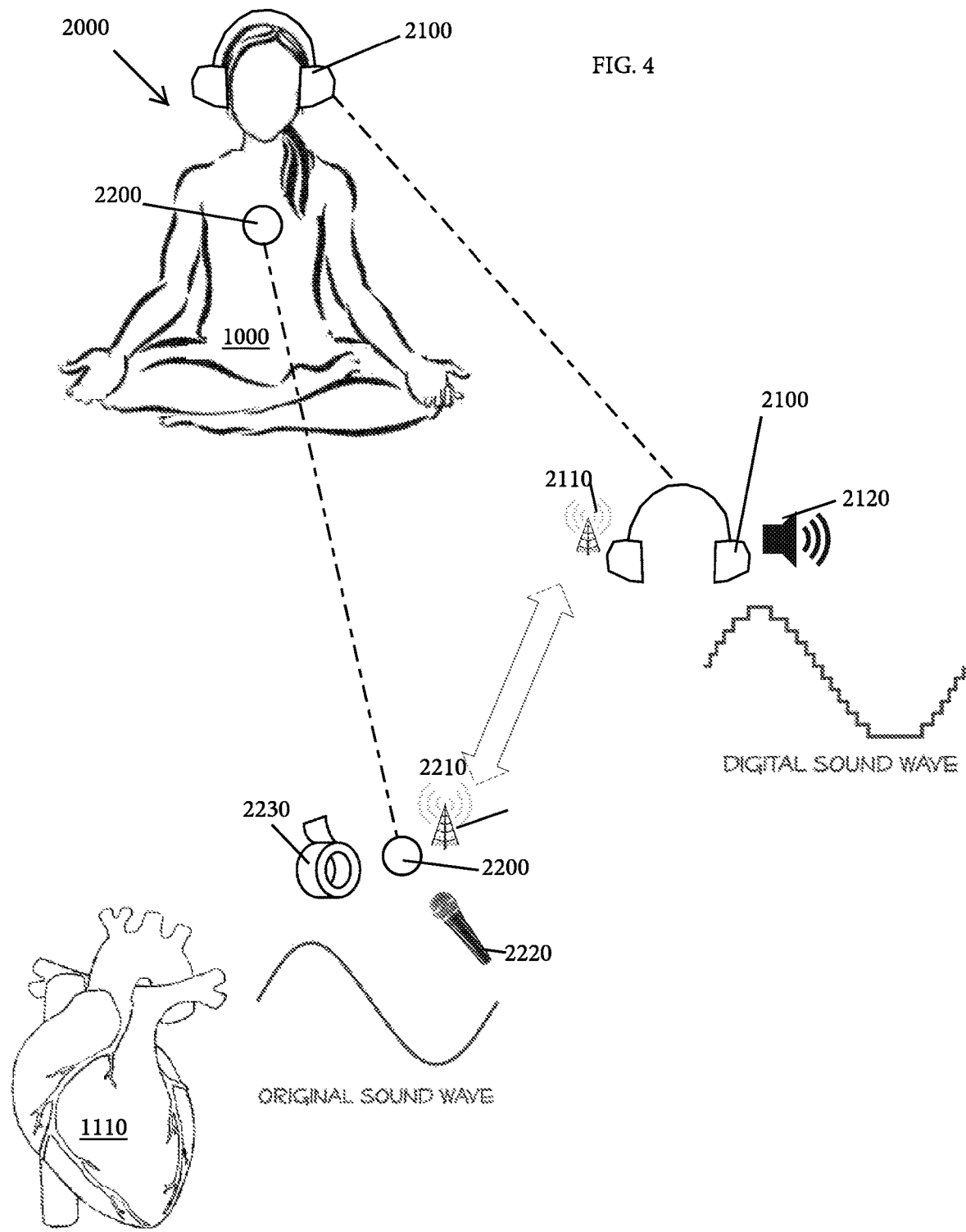
FIG. 4 is a schematic of the disclosed wireless and hands-free heart-beat audio transmitter and receiver system 2000 in position in the user 1000.

In one embodiment, the disclosed system is a device that allows a user to listen to his or her heartbeat wirelessly and hands-free during meditation and relaxation. FIG. 1 is a basic view of a user 1000 meditating, relaxing, or exercising. FIG. 2 is a basic view of the user 1000 meditating, relaxing, or exercising with a wireless and hands-free heart-beat audio transmitter and receiver system 2000 in position in the user 1000. FIG. 4 is a schematic of the disclosed wireless and hands-free heart-beat audio transmitter and receiver system 2000 in position in the user 1000. As shown, the system 2000 is defined by a heart monitor 2200 and headphones 2100.

Referring to FIG. 4, in a preferred embodiment, a heart-monitor 2200 may be placed over the heart with a skin-compatible adhesive 2230. Suitably, for the monitor 2200 to adhere to the chest of a user 1000, double sided self-adhesive tape may be used. Often, such tape and adhesive includes silicone, is reusable, and is latex-free. One suitable type of double sided tape can be purchased from Parafix at https://parafix.com/product-groups/double-sided-materials/double-sided-tape/.

Still referring to FIG. 4, suitably, the heart monitor may be defined by a microphone 2220 and transmitter 2210 for picking-up the hearts original sound wave input, converting the original sound wave to an electronic audio signal, transmitting an electrical audio signal wirelessly (e.g., by Bluetooth®) to headphones 2100 worn by the user 1000. In one instance, any one of several commercially available "mini" mics could be incorporated. For instance microphones purchased from Digi-key Electonics here: https://www.digikey.com/product-detail/en/sparkfun-electronics/BOB-12758/1568-1472-ND/6592307?WT.srch=1&gclid=Ci0KCQiwzlzWBRDnARIsAAkc8hHMsZ1B Mi9VEwb1ELM0ZI9qCL-hEMINckX4SOJ1igo46pac3-V28K4aAigNEALw wcB Suitably, the headphones 2100 feature a receiver 2110 and speaker 2120 that translates the audio signal to a digital sound output so that the listener can enjoy the sounds of his or her own beating heart 1110. Any style of commercially available headphones would be suitable for this application.

In another embodiment (not shown), the heart monitor 2200 includes a recorder and computer memory for storing a digital copy of the electronic audio signal for later transmission and playback of the headphones 2100.

Figure 3:
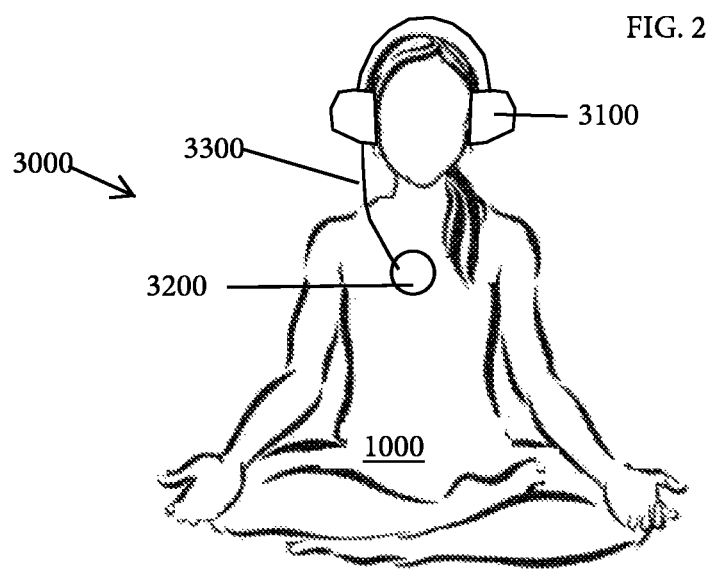
FIG. 3 is a basic view of the user 1000 meditating, relaxing, or exercising with a wired and hands-free heart-beat audio transmitter and receiver system 2000 in position in the user 1000.

FIG. 3 is a basic view of the user 1000 meditating, relaxing, or exercising with a wired and hands-free heartbeat audio transmitter and receiver system 3000 in position in the user 1000. In another embodiment, the heart monitor 3200 includes an audio jack 3300 for wired connection to the headphones 3100. Although wired, the system 3000 otherwise operates in accordance with the other disclosed embodiments of the system.

As shown in the figure, preferred uses for the system 2000/3000 include, but are not limited to:
1. mediation
2. relaxation
3. during workout—running, yoga, etc.
4. mother to wear for child to hear mother's heartbeat
5. general medical purposes In another embodiment (not shown), the disclosed system need not be adhered to the user's 1000 chest via an adhesive, but may instead be embedded directly in the user's clothing, i.e., their shirt. This embodiment allows for the user 1000 to remove and re-engage the system easily and quickly by simply removing or wearing a shirt with the heartrate monitor 2200 embedded therein. This embodiment is consistent with the principle that the device 2000/3000 is contemplated to operate in a hands-free manner.

In another embodiment, the system 2000/3000 optionally includes a software application ("app"), compatible with the user's mobile device or computer. Suitably, the application is configured with code that transfers the output data (e.g., a recorded heart beat) from the transmitter 2210 to a database and stores that data via a computer memory (e.g., a hard drive, SIM card or non-volatile or traditional ram (NVRAM or RAM)). In a preferred embodiment, software application may be configured to quantify the recorded heart beat into heart rate data (e.g., beats per minute or heart rate variability) and graphically display said data. Preferably, the user may view characteristics of their heartbeat and accompanying data during the recorded time period, said characteristics including but not limited to: heartrate variability over time, maximum heartrate, minimum heartrate, average heartrate, and the periods of time during which the user was most and least at rest. Data can be retrieved from the database and sent to a user via text message or email.

In one preferred embodiment, the software application is further configured for playback of the recorded heart beat sounds or a portion of the recorded heart beat sounds. In particular, a preferred embodiment of the application isolates portions of the recorded heart beat that manifest a high heart rate variability and plays-back, on demand, this portion of the user's heart beat to the user. Suitably, the application also permits the user to select a time range from a given stored recording and to play back to the user or a third party through an amplification means, such as headphones 2100 or a speaker system 2120, the original analog soundwave or the converted digital version recorded during the chosen time range. The application likewise allows the user or a third party—such as the a mother's child—to listen to the user's heartbeat via the amplification means in real time and to monitor the data as it is collected and/or stored in real time. Additionally, the application can be configured to display graphically the aforementioned heartrate data characteristics in real time as they are recorded.

In one embodiment, the application additionally comprises an integrated auditory supplement function. The function permits the user to play an audio file and either the real time or previously recorded heartbeat simultaneously via the same amplification means. One example of an audio file the user may select is a voice-guided meditation. By overlaying the voice-guided on the real time heartbeat, the user may enjoy a guided meditation and monitor their heartrate as to ensure optimal results.

Although the method and apparatus is described above in terms of various exemplary embodiments and implementations, it should be understood that the various features, aspects and functionality described in one or more of the individual embodiments are not limited in their applicability to the particular embodiment with which they are described, but instead might be applied, alone or in various combinations, to one or more of the other embodiments of the disclosed method and apparatus, whether or not such embodiments are described and whether or not such features are presented as being a part of a described embodiment. Thus the breadth and scope of the claimed invention should not be limited by any of the above-described embodiments.

Terms and phrases used in this document, and variations thereof, unless otherwise expressly stated, should be construed as open-ended as opposed to limiting. As examples of the foregoing: the term "including" should be read as meaning "including, without limitation" or the like, the term "example" is used to provide exemplary instances of the item in discussion, not an exhaustive or limiting list thereof, the terms "a" or "an" should be read as meaning "at least one," "one or more," or the like, and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that might be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases might be absent. The use of the term "assembly" does not imply that the components or functionality described or claimed as part of the module are all configured in a common package. Indeed, any or all of the various components of a module, whether control logic or other components, might be combined in a single package or separately maintained and might further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives might be implemented without confinement to the illustrated examples. For example, block diagrams and their accompanying description should not be construed as mandating a particular architecture or configuration.

All original claims submitted with this specification are incorporated by reference in their entirety as if fully set forth herein.

I claim:

1. A system comprising:

a database;

a heart monitor with a microphone, configured to pick-up a heartbeat sound wave and converting the original sound wave to an electronic audio signal and a transmitter, configured to transmit the electronic audio signal;

headphones with a receiver and speaker, configured to receive the transmitted electronic audio signal and replay the electronic audio signal for a user, while the user is meditating, relaxing, or working out after (i) the heartbeat sound wave is picked-up and then converted to the electronic audio signal by the microphone, (ii) the electronic audio signal is transmitted to the receiver of the headphones via the transmitter, and (iii) the electronic audio signal is converted back into a soundwave by the speaker; and a software application configured with code that transfers the electrical audio signal to the database for storage, and wherein the software application is further configured to quantify the electrical audio signal into heartbeat data, graphically display the heartbeat data, and allow the user to view characteristics of their heartbeat including heartrate variability over time, maximum heartrate, minimum heartrate, average heartrate, and the periods of time during which the user was most and least at rest, and wherein the software application is further configured to isolate portions of the electronic audio signal associated with increased heartrate variability over time, and transmit the isolated portions to the user while the user is meditating, relaxing, or working out.

2. The system of claim 1, wherein the database is further configured to store an audio signal of a pre-recorded voice or sound, and wherein the software application is further configured to overlay the audio signal of the pre-recorded voice or sound on the electronic audio signal so that both the audio signal of the pre-recorded voice or sound and the electronic audio signal are transmitted to the receiver of the headphones via the transmitter and then converted into soundwaves by the speaker.

3. The system of claim 2, wherein the pre-recorded voice or sound comprises a voice recording.

4. The system of claim 3, wherein the voice recording comprises a voice-guided meditation.

5. The system of claim 1, wherein the electronic audio signal is recorded before the electronic audio signal is transmitted to the receiver of the headphones via the transmitter.

6. The system of claim 1, wherein the isolated portions are recorded for later playback.

7. The system of claim 1, wherein the software application is further configured to isolate at least a time range of the electronic audio signal selected by the user.

8. The system of claim 1, wherein the heart monitor is embedded in a garment worn by the user.

* * * * *